United States Patent [19]

Keipert

[11] Patent Number: 5,059,701

[45] Date of Patent: Oct. 22, 1991

[54] METHODS FOR PREPARATION OF CYCLOPENTADIENYLIRON (II) ARENES

[75] Inventor: Steven J. Keipert, Oakdale, Minn.

[73] Assignee: Minnesota Mining and Manufacturing Company, St. Paul, Minn.

[21] Appl. No.: 585,865

[22] Filed: Sep. 20, 1990

[51] Int. Cl.$^5$ .............................................. C07F 15/02
[52] U.S. Cl. .......................................... 556/13; 556/1; 556/7; 556/27; 556/30; 556/143
[58] Field of Search ................... 556/143, 1, 7, 13, 30, 556/51, 27

[56] References Cited

U.S. PATENT DOCUMENTS

| | | | |
|---|---|---|---|
| 3,130,214 | 4/1964 | Coffield et al. | 556/13 |
| 3,468,921 | 9/1969 | Wilke | 556/143 X |
| 4,556,719 | 12/1985 | Boennemann et al. | 556/7 |
| 4,868,288 | 9/1989 | Meier | 534/15 |

FOREIGN PATENT DOCUMENTS 314618 10/1988 European Pat. Off. .

OTHER PUBLICATIONS

Journal of Organometallic Chemistry, 1977, vol. 3, p. 311.
Tetrahedron 1983, vol. 39, p. 4037.
Organic Syntheses Collective Value IV, Rabjohn, N., Ed.; Wiley, New York, 1963, p. 473.
Hawley's Condensed Chemical Dictionary, N. Irving Sife, Richard H. Lewis, Sr., 1987 (11th ed.), p. 858.
Journal of Organometallic Chemistry, 1976, vol. 111, p. 339.

Primary Examiner—Arthur C. Prescott
Attorney, Agent, or Firm—Gary L. Griswold; Walter N. Kirn; Carolyn V. Peters

[57] ABSTRACT

Two improved methods for preparation of compounds with the structure shown in equation X $$[(Cp)-Fe-(Ar)]^+{}_b X^{b-} \qquad (X)$$

where Cp is an eta$^5$ complexed, substituted or unsubstituted, cyclopentadienyl or indenyl anion, Ar is an eta$^6$ complexed substituted or unsubstituted, pi-arene ligand anad X is a b-valent anion where b is an integer between 1 and 3. The two methods, which differ in the source of the cyclopentadienyl anion - Lewis acid complex, utilize a Lewis acid assisted ligand transfer reaction. The cyclopentadienyl anion ligand, assisted by a Lewis acid is transferred to ferrous ion in the presence of an arene. In the first method, the cyclopentadienyl anion is derived from ferrocene and ferrous chloride. In this reaction, the cyclopentadienyliron (II) arene product is derived partially from ferrocene and partially from the ferrous salt. In the second method, the cyclopentadienyl anion - Lewis acid complex is formed by direct reaction of the Lewis acid with an inorganic cyclopentadienide salt. The cyclopentadienyliron (II) arene product of this reaction is derived entirely from the ferrous salt. Cyclopentadienyliron (II) arene cations are of great interest due to their utility as photoactivatable catalysts for a variety of polymerization reactions.

23 Claims, No Drawings

METHODS FOR PREPARATION OF CYCLOPENTADIENYLIRON (II) ARENES

The United States government has certain rights in this invention pursuant to Contract No. DE-AC7-88ID12692, entitled "Industrial Gaseous Waste Reduction Phase II" awarded by the United States Department of Energy.

BACKGROUND OF THE PRESENT INVENTION

1. Field of Invention

The present invention relates to improved methods for the preparation of organometallic complexes, more particularly, to the preparation of cyclopentadienyliron (II) arene complexes, useful as photoactivatable catalysts for a variety of polymerization reactions.

2. Background

Methods for preparation of cyclopentadienyliron (II) arene complexes rely almost exclusively on the ligand exchange reaction of eta-5-dicyclopentadienyliron (II) (commonly referred to as ferrocene) with a arene in the presence of a Lewis acid. This reaction is described by equation I

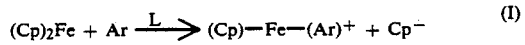

where Cp is the cyclopentadienyl anion, Ar is a arene and L is a Lewis acid.

This reaction reportedly involves removal of one cyclopentadienyl anion ligand from ferrocene by the Lewis acid as described and whose structures are given as examples in the *Journal of Organometallic Chemistry Library* 1977, 3, 311 and *Tetrahedron* 1983, 39, 4037. It is theorized that the referenced reaction produces a coordinately unsaturated cyclopentadienyliron (II) cation and a cyclopentadienyl anion-Lewis acid complex (anion-acid complex).

The cyclopentadienyliron (II) cation then coordinates the arene to give the cyclopentadienyliron (II) arene complex product. The cyclopentadienyl anion-Lewis acid complex undergoes further chemistry, the nature of which depends on the particular Lewis acid used. However, in none of the reactions known in the related art does this complex contribute to the formation of cyclopentadienyliron (II) arene cation.

The most commonly used Lewis acid for these reactions is aluminum chloride ($AlCl_3$). Additionally, aluminum bromide, gallium chloride, zirconium tetrachloride, hafnium tetrachloride, boron trifluoride and tin tetrachloride may also be used. Mixtures of zirconium or hafnium tetrachloride with aluminum chloride and titanium tetrachloride have also been described (See EP-A 314,618 and U.S. Pat. No. 4,868,288).

Furthermore, it has been reported that the ligand exchange reaction is often benefited by addition of a reducing metal. Using a reducing metal not only increases product yield, it advantageously reduces the amount of side reactions typically associated with ligand exchange. The most commonly used reducing metal is a finely divided aluminum powder. Examples and details of reactions using a reducing metal are illustrated in *Tetrahedron* 1983, 39, 4037. Reportedly, addition of a small amount of water to aluminum chloride catalyzed reactions can improve product yield. Id. at 4037.

When ligand exchange with aluminum chloride is performed pursuant to the prior art methods, the intermediate cyclopentadienyl anion (also referred to as a cyclopentadienide)-aluminum chloride complex (anion-acid complex) is unstable under the reaction conditions. Further reaction leads predominantly to polymeric material and ferrocene alkylation products. (See *Journal of Organometallic Chemistry*, 1976, 111, 339.)

However, when the Lewis acid used is zirconium or hafnium tetrachloride, the cyclopentadienide-Lewis acid complex (anion-acid complex) is converted to a stable, isolatable organometallic complex. For example, using zirconium tetrachloride leads to the formation of zirconocene dichloride. (See EP-A 314,618).

In several prior art references, the ferrous ion is used in related reactions. For example, the Tetrahedron article supra discloses, in a related reaction, that the ferrous or ferric ion, in the presence of a Lewis acid catalyst, can coordinate two molecules of a neutral arene to form a bis-arene iron (II) di-cation. This reaction is an example of the generally known Fischer-Haffner reaction. Id. at 4037. The Lewis acid most commonly used in the Fischer-Haffner reaction is aluminum chloride and is shown in equation II.

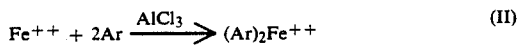

In another example, it is taught that ferrocenes may be prepared by reaction of cyclopentadienide salts with ferrous ion. This method of preparing ferrocene is described in *Organic Syntheses Collective Volume IV*, Rabjohn, N. Ed.; Wiley, New York, 1963, p. 473. The preparation of ferrocene as described and shown in equation III, is usually run using sodium cyclopentadienide and ferrous chloride in cold tetrahydrofuran. In this preparation method however, a Lewis acid catalyst is typically not required.

However, none of these prior art references teach transferring a cyclopentadienyl anion ligand from the Lewis acid complexes to a ferrous ion.

SUMMARY OF THE INVENTION

This invention describes two improved methods for preparation of a class of organometallic complex salts, in particular, cyclopentadienyliron (II) arene cation complex salts. Both methods utilize a cyclopentadienyliron (II) anion-Lewis acid complex as an intermediate. This complex provides a cyclopentadienyl anion ligand transfer to ferrous ion in the presence of a arene. The improved methods differ from each other in the source of the cyclopentadienyl anion-Lewis acid complex.

Briefly, this invention provides a first synthetic method for providing cyclopentadienyliron (II) arene complex, wherein the cyclopentadienyl anion is derived from ferrocene. In this reaction, the cyclopentadienyliron (II) arene product is derived partially from ferrocene and partially from an intermediate ferrous salt in a process comprising the steps:

1) providing a mixture of a ferrocene, a arene, a Lewis acid, optionally, an inert diluent, optionally, a reducing metal, and a sufficient amount of ferrous ion to complete a reaction; and 2) isolating the complex.

In another aspect, this invention provides a second synthetic method for providing Cp iron (II) arene, wherein a cyclopentadienyl anion-Lewis acid complex is formed by direct reaction of a Lewis acid with an inorganic cyclopentadienide salt. The cyclopentadienyliron (II) arene product of this reaction is derived entirely from the ferrous salt in a process comprising the steps:

1) admixing a metal cyclopentadienide salt having the structure represented by $M^{+b}(Cp^-)_b$, where M is a b-valent metal cation, and b is an integer 1, 2, or 3, a Lewis acid, arene, a ferrous salt, optionally, a reducing metal, optionally, an inert diluent; and 2) isolating the complex.

In another aspect, novel compositions containing cyclopentadienyl iron (II) arene complex salts in combination with at least one of ferrous and ferric ions are disclosed.

These complexes are useful as photoactivated catalysts for a variety of polymerization reactions. As used in this application:

"Ar" means an eta$^6$ complexed arene, which may be substituted as described hereinbelow.

"catalytically effective amount" means a quantity sufficient to effect polymerization of the polymerizable material at least to a degree to increase the viscosity of the composition;

"Cp" means an eta$^5$ complexed cyclopentadienyl anion or an eta$^5$ complexed indenyl anion, either of which may be substituted, as described hereinbelow.

"cyclopentadienyl anion" and "cyclopentadienide" are terms that are used interchangeably;

"ferrocene" means dicyclopentadienyliron (II), having a general formula (Cp)—Fe—(Cp)

where each Cp independently is a pi-arene anion;

"inert diluent" means any diluting liquid which does not interfere or participate in the above reactions, that is, is non-polar and non-reactive to the reaction;

"organometallic complex" means a chemical substance wherein at least one carbon atom of an organic group is directly bonded to at least one metal atom (Hawley's Condensed Chemical Dictionary, N. Irving Sife, Richard H. Lewis Sr. 1987 (11th ed.), p. 858); and "photoactivatable catalyst" or "photoinitiated catalyst" means a substance that effects or aids polymerization processes subsequent to exposure to light.

The present invention provides significant improvements over the known art methods that result from incorporation of a source of inorganic ferrous ion in reactions of the type shown in equation I.

Thus, for the first synthetic method, it is contemplated that in the presence of ferrous ion, a cyclopentadienyl anion from the starting material, ferrocene is transferred via from the Lewis acid complex to the ferrous ion, producing a cyclopentadienyliron (II) cation. The cation then coordinates a pi-arene ligand to form additional cyclopentadienyliron (II) arene cation product. The overall reaction is the efficient conversion of a molecule of ferrocene, a ferrous ion, and two pi-arene molecules into two molecules of cyclopentadienyliron (II) arene cation as is shown in equation IV below:

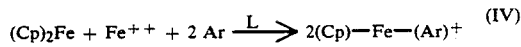
$$(Cp)_2Fe + Fe^{++} + 2\,Ar \xrightarrow{L} 2(Cp)\text{—}Fe\text{—}(Ar)^+ \qquad (IV)$$

For the second synthetic method, it is theorized that a cyclopentadienyl anion-Lewis acid complex is formed by direct reaction of a Lewis acid with a cyclopentadienide salt. Advantageously, the cyclopentadienyliron (II) arene product is derived solely from ferrous salt. The overall reaction is the conversion of a cyclopentadienyl anion, a ferrous ion and an arene molecule into a molecule of cyclopentadienyliron (II) arene cation as shown in equation V.

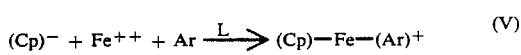
$$(Cp)^- + Fe^{++} + Ar \xrightarrow{L} (Cp)\text{—}Fe\text{—}(Ar)^+ \qquad (V)$$

DETAILED DESCRIPTION AND PREFERRED EMBODIMENTS OF THE INVENTION

Formation of a single cyclopentadienyliron (II) arene cation complex from ferrocene is observed in the prior art. In contrast, a first reaction method of the present invention results in a much more efficient use of ferrocene. Theoretically, twice the amount of product could be produced from a given amount of ferrocene. In practice, it has been found that significantly greater amounts of product are obtained when ferrous ion is present. Improvements are observed over control reactions run under the same conditions in the absence of ferrous ion.

In another aspect, this invention provides a second reaction method. However, the second reaction method does not use ferrocene as the starting material. Instead, the cyclopentadienyliron (II) arene cation is formed by direct reaction of a ferrous ion with a cyclopentadienyl anion and a pi-arene ligand. As in the first reaction method, the process is assisted by a Lewis acid.

The second reaction method of the present invention appears to be more than just the formation of ferrocene as described in equation III, followed by formation of cyclopentadienyliron (II) arene cation by a known method. Typically, in the prior art, a significant amount of unreacted ferrocene remains at the end of the reaction. Lack of ferrocene by-product in the second reaction method suggests that ferrocene is not an intermediate in the process. The only discernible by-product from the second reaction appears to be a water insoluble polymer. It is suggested that this water insoluble polymer is derived from the cyclopentadienide salt.

In reactions using the first method of preparation the cyclopentadienyl anion is derived from ferrocene. The cyclopentadienyliron (II) arene product is derived partially from ferrocene and partially from a ferrous salt. This reaction is illustrated in equation IV above.

In the reactions of the first method, removal of one cyclopentadienyl ligand from a molecule of ferrocene by a Lewis acid produces a cyclopentadienyl anion-Lewis acid complex (anion-acid complex) and a cyclopentadienyliron (II) cation. The cyclopentadienyliron (II) cation complexes an arene in a manner known in the prior art to form the cyclopentadienyliron (II) arene cation product. The cyclopentadienyl anion-Lewis acid complex also transfers a cyclopentadienyl anion to a ferrous ion obtained from a ferrous salt. This transfer is then followed by arene complexation, producing additional product in a manner not heretofore known.

In reactions using the second method, the cyclopentadienyl anion-Lewis acid complex is formed by direct reaction of a Lewis acid with an inorganic cyclopentadienide salt. The cyclopentadienyl ligand is then transferred to a ferrous ion in a manner not previously known in the prior art. The cyclopentadienyliron (II) arene product of this reaction is derived entirely from the ferrous salt as illustrated by equation V above.

Both of these reaction types differ from the prior art in that they utilize ferrous ion as a source of iron to form the end product. All the preparation methods of the compounds known in the prior art use some form of organo-iron compound, typically ferrocene, as the iron source. Substitution of inexpensive ferrous salts for some or all of the ferrocene results is a significant advantage in production cost effectiveness.

While not wishing to be bound by an exact reaction mechanism, it is hypothesized that the initial step in both of these reactions is formation of a cyclopentadienyl anion-Lewis acid complex. This complex then transfers the cyclopentadienyl anion to a ferrous ion forming a cyclopentadienyliron (II) cation. The cation then coordinates with a pi-arene to give the cyclopentadienyl-iron (II) arene cation complex product. The two reactions of the present invention differ in the source of the cyclopentadienyl anion-Lewis acid complex.

A reaction sequence of the first method hypothesized to be involved in the production of the cyclopentadienyl iron (II) arene cation complex is as follows:

$$(Cp)-Fe-(Cp) + L \longrightarrow (Cp)-L^- + (Cp)-Fe^+ \quad (A)$$

$$(Cp)-L^- + Fe^{++} \longrightarrow (Cp)-Fe^+ + L \quad (B)$$

$$2(Cp)-Fe^+ + 2Ar \longrightarrow 2(Cp)-Fe-(Ar)^+ \quad (C)$$

where equation A illustrates abstraction of a cyclopentadienyl anion from ferrocene by a Lewis acid (L); equation B illustrates the transfer of a cyclopentadienyl anion from the Lewis acid (L) to a ferrous ion ($Fe^{++}$); and equation C illustrates the complexation of the arene (Ar) by the cyclopentadienylrion (II) cation (($Cp$)-$Fe^+$) to form the cyclopentadienylrion (II) arene cation (($Cp$)-$Fe$-($Ar$)$^+$).

Finally, equation D illustrates the overall reaction, wherein 2 moles of cyclopentadienyliron (II) arene cation is produced.

$$(Cp)-Fe-(Cp)+Fe^{++}+2Ar\rightarrow 2(Cp)-Fe-(Ar)^+ \quad (D)$$

Likewise, a reaction sequence of the second method hypothesized to be involved in the production of the cyclopentadienyliron (II) arene cation complex is as follows:

$$(Cp)^- + L \longrightarrow (Cp)-L^- \quad (E)$$

$$(Cp)-L^- + Fe^{++} \longrightarrow (Cp)-Fe^+ + L \quad (F)$$

$$(Cp)-Fe^+ + Ar \longrightarrow (Cp)-Fe-(Ar)^+ \quad (G)$$

where equation E illustrates the complexation of an inorganic cyclopentadienide salt by a Lewis acid (L), and equations F and G are described similarly to equations B and C, respectively, of the first method wherein a cyclopentadienyl iron (II) arene cation is produced from an intermediate cyclopentadienyl anion-Lewis acid complex as in the first reaction method. In summation, equation H illustrates the overall reaction.

$$(Cp)^- + Fe^{++} + Ar \rightarrow (Cp)-Fe-(Ar)^+ \quad (H)$$

In a more general description of the invention, invention describes a method for preparing compounds with the structure shown in formula VI $$[(Cp)-Fe-(Ar)]^+{}_b X^{b-} \quad (VI)$$

where Cp is an eta5 complexed, substituted or unsubstituted, cyclopentadienyl or indenyl anion, Ar is a eta$^6$ complexed, substituted or unsubstituted, pi-arene ligand, and X is a b-valent anion where b is an integer 1, 2 or 3.

Possible pi-arene ligands, Ar, include aromatic groups of from 6 to 100 carbon atoms, as well as heteroaromatic groups of from 3 to 100 carbon atoms, and 1 to 10 heteroatoms, particularly those containing non-peroxidic oxygen, nitrogen or sulfur heteroatoms, alone, or in combination. The aromatic groups may be mononuclear, condensed polynuclear or non-condensed polynuclear. Aromatic groups may be unsubstituted, monosubstituted or polysubstituted with identical or different monovalent radicals such as halogens, straight or branched chain alkyl or fluoroalkyl, phenyl or other aryl, alkoxy, aryloxy, alkylthio, arylthio, cyano, alkanoyl, benzoyl, or carboxylic acid ester. The pi-arene may be a pure compound or a mixture of several compounds.

Suitable pi-arene ligands include for example: benzene, toluene, o-xylene, m-xylene, p-xlene, mixed isomer xylene, mesitylene, durene, ethylbenzene, diethylbenzenes, propylbenzene, hexamethylbenzene, cumene, diisopropylbenzene, isobutylbenzene, chlorobenzene, p-dichlorobenzene, bromobenzene, p-chlorotoluene, anisole, ethoxybenzene, p-dimethoxybenzene, naphthalene, methylnapththalenes, chloronaphthalenes, bromonaphthalenes, methoxynaphthalenes, 1,2-dihydronaphthalene, 1,2,3,4-tetrahydronaphthalene, biphenyl, diphenylmethane, triphenylmethane, diphenyl ether, diphenyl sulfide, stilbene, biphenylene, paracyclophane, anthracene, phenanthrene, 9,10-dihydroanthracene, fluorene, triphenylene, pyrene, perylene, chrysene, chromene, coronene, naphthacene, xanthene, thioxanthene, pyridine, picolines, quinoline, quinaldine, pyrrole, furan, benzofuran, dibenzofuran, benzopyran, carbazole, thiophene, benzothiophene, indole, indene, acridine, and benzoxazine. Other examples of suitable aromatic compounds that may function as an aryl ligand may be found by consulting any of many chemical handbooks.

Possible pi-arene ligand substituents include for example: chloro, bromo, methyl, ethyl, propyl, isopropyl, n-butyl, sec-butyl, tert-butyl, isobutyl, n-pentyl, n-hexyl, 2-ethylhexyl, n-octyl, methoxy, ethoxy, n-propoxy, isopropoxy, n-butoxy, phenoxy, methylthio, ethylthio, n-propylthio, isopropylthio, n-butylthio, carboxylic acid methyl, ethyl, propyl, isopropyl, and n-butyl esters, acetyl, propionyl, butyryl, and cyano.

Cp is a eta$^5$ bound pi-arene anion. This may be an unsubstituted, monosubstituted, or polysubstituted cyclopentadienyl or indenyl anion. Substituents may be the same or different monovalent radicals such as straight chain or branched alkyl or fluoroalkyl having 1 to 10 carbon atoms, aryl, 1-10 carbon carboxylic acid ester or alkanoyl, benzoyl, chloro or cyano.

The preferred pi-arene anions are unsubstituted indenyl and cyclopentadienyl anions, especially cyclopentadienyl anion. However, other suitable examples include the anions of methylcyclopentadiene, ethylcyclopentadiene, n-propylcyclopentadiene, n-butylcyclopentadiene, isobutylcyclopentadiene, 1,2-dimethylcyclopentadiene, 1,3-dimethylcyclopentadiene, trifluoromethylcyclopentadiene, phenylcyclopentadiene, cyclopentadienecarboxylic acid methyl and ethyl esters, acetylcyclopentadiene, benzoylcyclopentadiene, chlorocyclopentadiene, and cyanocyclopentadiene.

Suitable anions, $X^{b-}$, include the chlorinated, fluorinated, hydroxylated, alkylated, and arylated anions of P, As, Sb, Bi, B, Al, Ga, In, Sc, Ti, Zr, V, Cr, Mn, Fe, Co, Cu, Zn, Sn, and Ce. In the case of anions containing alkyl or aryl groups, the groups may be substituted or unsubstituted. Illustrative examples of other suitable anions include: $(phenyl)_4B^-$, $(phenyl)_3(alkyl)B^-$, $(alkyl)_4B^-$, where alkyl can be ethyl, propyl, butyl, isobutyl, hexyl, and the like, $(phenyl)_3(benzyl)B^-$, $BF_4^-$, $PF_6^-$, $AsF_6^-$, $SbF_6^-$, $FeCl_4^-$, $SnCl_5^-$, $AlF_4^-$, $GaCl_4^-$, $TiCl_4^-$, $SbF_5OH^-$. Preferably, the anions are $BF_4^-$, $PF_6^-$, $SbF_6^-$, $SbF_5OH^-$, $AsF_6^-$, and $SbCl_6^-$. Additional suitable anions, $X^{b-}$, include the organic sulfonates. Illustrative of suitable sulfonate-containing anions are methanesulfonate, trifluoromethanesulfonate, benzenesulfonate, p-toluenesulfonate, p-chlorobenzenesulfonate, p-trifluoromethylbenzenesulfonate, and the like. Trifluoromethanesulfonate is preferred.

Additional suitable anions include the anions of strong acids such as perchlorate, sulfate, and nitrate.

The following sections describe many of the reaction parameters applicable to both the first and second methods of preparation. These are further illustrated in several examples discussed below. However, the parameters and the examples are meant as illustrations of the present invention and in no way be construed to limit the present invention.

In reactions of the first method described in the present invention, compounds described in structure VI are prepared from ferrocene or ferrocene derivatives described by structure VII,

—Fe—     (VII)

where each Cp independently is a pi-arene anion as described above. Whenever the compound ferrocene is referred to in this invention, this should be understood to include all of the ferrocene derivatives described by structure VII. In addition to ferrocene, the reaction takes place in the present of the following ingredients. The indicated amounts are based on 1 mole of ferrocene.

At least 2 moles of arene as described earlier. It is preferable to use a 5-10 fold molar excess of arene. The arene is often used as the reaction solvent, if it is a liquid at the desired reaction temperature.

At least 0.2 mole of a ferrous salt, with 1 mole being the preferred amount.

At least 1 mole of Lewis acid, preferably between 1.5 and 3 moles, as either a single compound or as a mixture of two or more compounds.

Optionally, 0.1 to 1 mole of a reducing metal. Finely divided aluminum power is preferred.

Optionally, an inert, non-polar solvent such as an alkane or cycloalkane which is liquid at the reaction temperature.

As little moisture as possible should be present in the reaction. While it is preferred that the reaction be run under anhydrous conditions, such as in the inert atmosphere of dry nitrogen, it is possible to run the reaction under normal atmospheric conditions.

All the ingredients may be added, in any order. The reaction components are mixed and the reaction is typically initiated by heating. The source of initiation heat may either be internal, that is an exothermic reaction or external, for example using a heating mantle. In reactions that are very rapid or exothermic, it may be advantageous to combine the reactants slowly. For example, slow addition of the ferrocene to the remaining reactants may be recommended.

The reaction may be run at temperatures between 20 and 250 degrees Celsius (C), with temperatures between 80° and 140° C. being preferred. Duration of the reaction may vary from between 0.1 and 24 hours, with a duration time of 2 to 6 hours being preferred. The temperature ranges and duration times are variable and dependent on the starting ingredients, as illustrated in the examples below.

The reaction end is typically determined by yield percent of reaction product. However, any means known in the art to ascertain reaction completion may be applicable. Upon completion of the reaction, the reaction product or mixture is cooled and quenched, typically by Lewis acid hydration.

The reaction may be quenched by slowly adding water, alcohol-water mixtures or absolute alcohols followed by water. External cooling is simultaneously applied to the reaction vessel. A preferred method is addition of an absolute alcohol such as methanol, ethanol or isopropanol, followed by addition of water. A more preferred reaction quench method involves addition of 0.5 liter of absolute ethanol per mole of ferrocene at a rate such that the temperature is maintained at approximately 60 degrees and below. The reaction mixture is then transferred into an ice/water mixture wherein 2 liters of ice/water per mole of ferrocene is used. The ice/water mixture results in a two-phase mixture. The desired end product is contained in the aqueous phase.

It is sometimes advantageous to add a mild reducing agent to the product at this point to reduce any ferrocenium ion that may have been formed. The reducing agent reduces the ferrocenium ion back to ferrocene. Generally, ascorbic acid as a reducing agent is preferred. However, sodium sulfite may also be used as a reducing agent.

It is also often advantageous to filter the reaction product at this point to remove any residual reducing metal powders that may complicate phase separation.

The resultant mixture of an aqueous phase and an organic phase is then separated. The aqueous phase, containing the product, is extracted with a suitable organic solvent or solvent mixture. The extraction removes any impurities present. Preferred extraction solvents are non-polar, water-immiscible solvents that dissolve ferrocene and arene. Examples of preferred solvents include cyclohexane and dichloromethane. The resulting aqueous solution generally contains the product as its halide, or halide-Lewis acid complex salt, for example $AlCl_4^-$ and the like.

It is often desirable to exchange anions at this point to provide a product with non-nucleophilic anions that are functionally more useful as photoinitiable polymerization catalysts. For example, nucleophilic anions such as $Cl^-$ interfere with the action of the photocatalyst by complexing the iron and preventing monomer complexation. Non-nucleophillic anions such as $PF_6^-$, $SbF_6^-$, $BF_4^-$ are preferred for their higher activity as catalysts. Although the ion exchange may proceed as indicated hereinabove, the ion exchange may be done by any process known in the art and still be within the spirit and scope of the present invention.

The desired anion-exchanged product can often be precipitated by addition of a water soluble salt of the desired anion. Examples may include precipitation of hexafluorophosphate salts ($PF_6^-$) by addition of ammonium, sodium or potassium hexafluorophosphates or hexafluorophosphoric acid, or hexafluoroantimonate salts ($SbF_6^-$) by sodium hexafluoroantimonate, or tetrafluoroborate salts by tetrafluoroboric acid.

The desired product may also be removed by extraction with a suitable organic solvent, such as dichloromethane. This anion exchange method is particularly advantageous when the product has appreciable water solubility.

Ferrous salts used in the reaction include all of those which have sufficient solubility in the reaction medium, or sufficient surface reactivity to serve as Cp acceptors; that is, they react with the Lewis acid-Cp complex. However, it is necessary that the anion component of the ferrous salt not successfully compete with the Cp anion. The anion component should be of low enough basicity that it does not complex the ferrous ion so strongly that the anion cannot be displaced by the arene and cyclopentadienyl anion ligands with assistance of the Lewis acid. The ferrous salt should also be in an anhydrous, or nearly anhydrous form and not contain functionality sufficiently acidic to protonate the cyclopentadienyl anion.

The preferred ferrous salt is ferrous chloride. However, other suitable ferrous salts examples may include fluoride, chloride, bromide, iodide, sulfate and nitrate salts.

In a particularly preferred technique, ferrous chloride is prepared just prior to the reaction by heating anhydrous ferric chloride with the arene that will be used in the reaction. Once ferrous chloride formation is complete, the other reactants are added. The reaction then proceeds as taught in Example 4.

In another preferred technique, ferrous chloride is prepared by heating anhydrous ferric chloride at reflux in chlorobenzene for 3 hours. The resultant ferrous chloride produced is removed by filtration, rinsed with the appropriate arene to remove residual chlorobenzenes, and added wet, that is "wetted" with arene, to the desired reaction mixture. The reaction using ferrous chloride is then run as illustrated in the examples below.

It is also known that ferrous chloride may be prepared prior to the primary reaction run by reacting anhydrous ferric chloride with powdered metallic iron.

The Lewis acid component of the reaction may be a single compound or a mixture of two or more compounds. When a single Lewis acid is used, it forms a complex with Cp anion that is sufficiently reactive under the reaction conditions to transfer the Cp anion to a ferrous ion. The preferred Lewis acid is selected from a first group of Lewis acids including the aluminum halides, especially the chloride and bromide, boron trifluoride and gallium halides, wherein sublimed aluminum chloride is most preferred.

A second group of Lewis acids include tetrachlorides of tin, titanium, zirconium and hafnium. They are generally unsuitable for use alone because they are more reactive than the acids of the first group. They tend to form stable intermediate product complexes with the Cp anion prior to the final product-Cp reaction with the ferrous ion.

However, mixtures of the Lewis acids from the first group with small amounts of more reactive Lewis acids of the second group, as a rate enhancing additive, may be used. Quantities of between 0 and 0.2 mole of the more reactive Lewis acids, with respect to the quantity of ferrocene used are preferred, with 0.1 mole being most preferred.

The technique of using a mixture of Lewis acids is particularly advantageous when preparing compounds that are difficult to prepare in high yield and purity using aluminum chloride alone. In a particularly useful embodiment cyclopentadienyliron (II) cumene cation can be prepared using a mixture of 3 moles of aluminum chloride and 0.1 mole of zirconium tetrachloride. This technique is taught in Example 5.

A reducing metal may be added to the reaction mixture as an antioxidant. The preferred reducing metal is aluminum powder. It is preferred that the metal be in a finely divided form to give a large surface area. However, other reducing metals known in the art, such as magnesium and zinc are also useful in the reactions. Other antioxidants that are capable of withstanding high reaction conditions may also be considered to be within the scope of the present invention.

It is preferred that the reaction be run using the arene as the reaction liquid or diluent. In cases where this is not feasible due to, for example, high arene cost, an inert diluent may be used. Useful diluents are those that are non-basic enough to avoid Lewis acid complexation and do not compete with the arene for complexation to iron. The preferred diluents are non-polar and non-reactive liquids, for example, alkanes and cycloalkanes, either as pure compounds or as mixtures.

Examples of an inert diluent include cyclohexane, methylcyclohexane, decahydronaphthalene, heptane, octane and similar straight chain and branched alkanes, as well as mixtures such as a commercial octane fraction. Aromatic liquids such as benzene, toluene, chlorobenzene, xylene and the like may be used in cases where the arene is sufficiently electron-rich to preclude competitive iron complexation by diluent.

In the second reaction method described in the present invention, compounds described in equation VI are prepared from metal cyclopentadienide salts having the structure VIII.

$$M^{b+}(Cp)_b^- \tag{VIII}$$

where M is a metal cation, such as Group IA of Periodic Table alkali metals and IIA Groups of Periodic Table alkaline earths, having a valence b, wherein b is an integer 1, 2 or 3, and Cp is a cyclopentadienyl anion as described previously.

In addition to the metal cyclopentadienide, the reaction takes place in the presence of the following ingredients. The ingredient amounts are based on 1 mole of the metal cyclopentadienide.

At least 1 mole of a arene as described earlier. It is preferable to use a 2-5 fold molar excess of the arene.

The arene is often used as the reaction solvent if it is a liquid at the desired reaction temperature.

At least 0.5 mole, and preferably 1 mole of a ferrous salt as described previously.

At least 0.5 mole of a Lewis acid, preferably between 1 and 3 moles, and most preferably 2 moles.

Optionally, from 0.1 to 1 mole of a reducing metal. Finely powdered aluminum metal is preferred.

Optionally, an inert diluent such as an alkane or cycloalkane, which is liquid at the reaction temperature.

It is preferable to run the reaction under an inert atmosphere such as dry nitrogen, although the reaction may be carried out in dry air. Preferably, the reaction is run under anhydrous or nearly anhydrous conditions to avoid protonation of the cyclopentadienyl anion.

All of the ingredients may be added, in any order, and the reaction initiated by heating. In reactions which are very rapid or exothermic, it may be advantageous to combine reactants slowly during the reaction. For example, slow addition of the metal cyclopentadienide to a mixture of the remaining reactants is recommended.

The reaction may be run at temperatures between 20° and 250° C., with temperatures between the range of 80° and 140° C. being preferred.

Duration of the reaction may vary from 0.1 to 24 hours. The preferred duration of the reaction is in the range of 2 to 6 hours. As indicated in the first reaction method, the temperature ranges and durations time are variable and dependent upon the starting ingredients used.

Alkali and alkaline earth metal cyclopentadienide salts may be used. Lithium, sodium and potassium are the preferred alkali metals, while magnesium is the preferred alkaline earth metal.

Upon completion of the reaction, the reaction product or mixture is cooled and quenched by the same techniques described for reactions of the first reaction method of preparation.

Similarly, a two-phase mixture is obtained. The resultant aqueous phase containing the desired product is separated from the two phase mixture. The aqueous phase may then be filtered to remove any polymeric products and residual reducing metal powder, if they are present. The aqueous solution may also be extracted with an organic solvent to remove organic soluble impurities. Unlike the first reaction method, extensive extraction of the aqueous solution is generally not required in the second reaction method.

Anion exchange may be carried out at this time, using the same techniques that were described previously for reactions of the first method of preparation.

The ferrous salts useful for this reaction are the same as those described earlier for the first method of preparation. Anhydrous ferrous chloride is the preferred ferrous salt and is commercially available or prepared using any of the techniques described earlier.

Lewis acids that may be used include any of those that do not form complexes with cyclopentadienyl anion, which are stable under the reaction conditions and are able to transfer cyclopentadienyl anion to ferrous ion. These include aluminum halides, especially the chloride and bromide, boron trifluoride and gallium halides, with aluminum chloride being the Lewis acid of choice.

Reducing metals described for reactions of the first method may also be optionally used in these reactions. Finely divided aluminum is preferred.

The same solvents or diluents described for reactions of the first kind may optionally be used in these reactions, and the same requirements apply. It is preferred to use the arene as the reaction solvent whenever possible.

It is known that any of the organometallic complex cations prepared using the present invention are useful as photoactivatable catalysts for a variety of polymerization reactions including polymerization of polyols and polyisocyanates to provide polyurethanes; epoxides to provide epoxy resins, cyanates to provide polytriazines; and vinyl ethers to provide polyvinyl ethers.

For example, polymerization of polyurethane precursors with the ionic salt of an organometallic complex cation can be carried out at room temperature for the majority of polyurethane precursors, although low temperature (e.g., $-10°$ C.) or elevated temperature (e.g., 30° to 200° C., preferably 50° to 150° C.) can be used to subdue the exotherm of polymerization or to accelerate the polymerization, respectively. Temperature of polymerization and amount of catalyst will vary and be dependent on the particular polyurethane precursors used and the desired application of the polymerized or cured product. The amount of ionic salt of an organometallic complex cation to be used as a catalyst should be sufficient to effect polymerization of the polyurethane precursors (i.e., a catalytically-effective amount) under the desired use conditions. Such amount generally will be in the range of about 0.01 to 20 weight percent, preferably 0.1 to 5.0 weight percent, and most preferably 0.5 to 2.0 weight percent, based on the weight of polyurethane precursors.

Polyurethane precursors include: polyisocyanates and isocyanate-reactive group-containing compounds. Examples of isocyanate-reactive group-containing compounds include: polyesters, carboxylic acids and their derivatives, polyhydric alcohols, polyethers, some polythioethers, polyacetals, polycarbonates, polyhydroxy (meth) acrylic resins, polyester amides and polyamides.

A more complete list of examples of polyisocyanates and isocyanate reactive group containing compounds that are useful is described in U.S. Pat. No. 4,740,577 and is incorporated into this application by reference.

In general, polymerization of cationically-sensitive monomers can be carried out as described above in the example of polyurethane polymerization.

Examples of polymerizable materials that can be cured or polymerized by the organometallic complex cation produced using the present invention include 1,2-, 1,3-, and 1,4-cyclic ethers, vinyl ethers, N-vinyl compound such as pyrrolidone, ethylenically unsaturated hydrocarbons, cyclic formals and cyclic organo siloxanes. An extensive list of cationically polymerizable monomers are given in U.S. Pat. Nos. 3,347,676 and 3,842,019 and European Patent Office (EPO) Application No. 364,073, wherein the EPO Application is incorporated into this application by reference.

Additionally, the complex cations are useful in two-stage polymerization (curing). The curing process proceeds by first activating an initiator and then heat-curing the activated precursors so obtained. The irradiation temperature ideally is below the temperature employed for the subsequent heat-curing. These activated precursors may normally be cured at temperatures that are substantially lower than those required for direct heat-curing, with advantage in the range from 50° to 110° C. This two-stage curing also makes it possible to control the polymerization in a particularly simple and advantageous manner.

Aspects and advantages of this invention are further illustrated by the following examples. The specific details are set forth to provide a more thorough understanding of the present invention. However, the particular materials and amounts thereof recited in these examples, as well as other conditions and details, should not be construed to unduly limit this invention. In other instances, well known processes and reactants have not been described in detail in order not to unnecessarily obscure the present invention.

EXAMPLES

All reactions described were run in either 1 or 2 liter reaction kettles. Reaction mixtures were heated with a thermostatically controlled heating mantle as a heating means. Reaction mixtures were cooled in an ice/water bath as the cooling means. Both the heating means and the cooling means may be other than specified here and still be within the spirit and scope of the present invention. The reaction kettle was also equipped with a mechanical stirrer, reflux condenser, addition funnel, and nitrogen inlet. All ingredients in the following examples are commercially available and may be obtained from any chemical supplier, such as Aldrich Chemical Co., Inc. of Milwaukee, Wisconsin.

Examples 1 and 3-6 were run according to the first method of preparation, while examples 7-9 were run according to the second method of preparation. The reaction product of the illustrative examples were confirmed by proton NMR.

EXAMPLE 1

Cyclopentadienyliron (II) (mixed isomer xylene) hexafluorophosphate was prepared from ferrocene and ferrous chloride according to the following reactions:

$$(C_5H_5)_2Fe + FeCl_2 + 2C_8H_{10} \xrightarrow{\frac{AlCl_3}{Al}}$$

$$2(C_5H_5)Fe(C_8H_{10})^+ AlCl_4^-$$

$$2(C_5H_5)Fe(C_8H_{10})^+ AlCl_4^- \xrightarrow{2HPF_6} 2(C_5H_5)Fe(C_8H_{10})^+ PF_6^-$$

To the reaction kettle described above, 46.5 grams (0.25 mole) of ferrocene, 6.75 grams (0.25 g. atom) of powdered aluminum, 100 grams (0.75 mole) of anhydrous aluminum chloride, 31.7 grams (0.25 mole) of anhydrous ferrous chloride, and 200 ml of mixed isomer xylene were added. The reaction mixture was stirred, purged with nitrogen, and heated to 140° C. for 5 hours.

The reaction mixture was then cooled in an ice/water bath and quenched by the slow addition of 200 ml of absolute ethanol. The reaction mixture was then transferred to a flask containing 1 liter of ice/water and 5 grams of ascorbic acid. The aqueous phase, containing the reaction product, was separated and extracted with three 200 ml portions of cyclohexane to remove impurities and unreacted starting material. The reaction product remaining in the aqueous phase was precipitated as its hexafluorophosphate salt by addition of 140 ml of 60% hexafluorophoshoric acid. This salt was redissolved and isolated by extraction with 500 ml and 100 ml portions of dichloromethane. The reaction product was crystallized from the combined dichloromethane extracts by addition of 1 liter of cyclohexane. The crystallized solids were removed by vacuum filtration, rinsed with cyclohexane, and dried under vacuum to yield 146 grams (0.39 mole) of product, giving a yield of 157% based on ferrocene, or 78% based on total iron.

COMPARATIVE EXAMPLE 2

Control reaction for Example 1 was run in the absence of ferrous chloride, with 1 equivalent of water. These are the known art reaction conditions giving the highest yields for this reaction:

$$(C_5H_5)_2Fe + C_8H_{10} \xrightarrow{\frac{AlCl_3/H_2O}{Al}} (C_5H_5)Fe(C_8H_{10})^+ AlCl_4^-$$

$$(C_5H_5)Fe(C_8H_{10})^+ AlCl_4^- \xrightarrow{HPF_6} (C_5H_5)Fe(C_8H_{10})^+ PF_6^-$$

To the reaction kettle described above were added 93 grams (0.5 mole) of ferrocene, 14 grams (0.5 g. atom) of powdered aluminum, 200 grams (1.5 mole) of anhydrous aluminum chloride, and 400 ml of mixed isomer xylene. The reaction mixture was stirred, purged with nitrogen and 9 grams (0.5 mole) of water were added. The reaction product was slowly heated to 140° C., during which time it produced a considerable reaction exotherm. After 6 hours, the reaction mixture was cooled in an ice/water bath and quenched by the slow addition of 400 ml of absolute ethanol.

The reaction mixture was transferred into a flask containing 1 liter of ice/water and 4 grams of ascorbic acid. The aqueous phase was separated and the organic phase was extracted with 200 ml of water. The combined aqueous solutions were extracted with four 250 ml portions of cyclohexane. The reaction product remaining in the aqueous phase was precipitated as the hexafluorophosphate salt by addition of 140 ml of 60% hexafluorophosphoric acid. This salt was redissolved and isolated by extraction with 500 ml and 100 ml portions of dichloromethane. The reaction product was crystallized from the combined dichloromethane solutions by addition of 750 ml of cyclohexane. The crystallized solids were removed by vacuum filtration, rinsed with 1:1 cyclohexane:dichloromethane, and dried under vacuum. Approximately 174.5 grams of product were obtained, for a yield of 94% based on ferrocene.

COMPARATIVE EXAMPLE 3

Reaction was run under the same conditions as Example 1, but using ferrous chloride hydrate to demonstrate the importance of anhydrous reaction conditions, according to the following reaction:

$$(C_5H_5)_2Fe + FeCl_2 \cdot 2H_2O + C_8H_{10} \xrightarrow{\frac{AlCl_3}{Al}}$$

$$(C_5H_5)Fe(C_8H_{10})^+ AlCl_4^-$$

$$(C_5H_5)Fe(C_8H_{10})^+ AlCl_4^- \xrightarrow{HPF_6} (C_5H_5)Fe(C_8H_{10})^+ PF_6^-$$

The reaction was run as in Example 1 except that 40.7 grams (0.25 mole) of ferrous chloride dihydrate was substituted for the anhydrous ferrous chloride, and the amount of xylenes was increased to 400 ml to improve stirring. Reaction time was 6 hours. The reaction was quenched with ethanol as in Example 1. The reaction mixture was then transferred to a flask containing 500 ml of ice/water and 4 grams of ascorbic acid. The aqueous phase was separated and the organic phase extracted with 150 ml of water. The aqueous solutions were combined and extracted with four 150 ml portions of cyclohexane. The reaction product was precipitated from the combined aqueous solution by addition of 140 grams of 60% hexafluorophosphoric acid. The reaction product was redissolved and isolated by extraction with one 300 ml, and two 100 ml portions of dichloromethane. From the combined dichloromethane solutions, the product was crystallized by addition of 600 ml of cyclohexane. The crystalline solids were then removed by vacuum filtration, and dried under vacuum. Approximately 80.9 grams (0.22 mole) of product were obtained, or a yield of 87% based on ferrocene.

EXAMPLE 4

Demonstration of a reaction to prepare cyclopentadienyliron (II) (mixed isomer xylene) xylene hexafluorophosphate from ferrocene and ferrous chloride. As shown in Step 1, the ferrous chloride was generated from ferric chloride prior to reaction.

$$2FeCl_3 + C_8H_{10} \rightarrow 2FeCl_2 + C_8H_9Cl + HCl \quad \text{(Step 1)}$$

The reaction equations were:

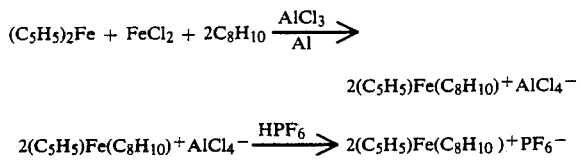

To the reaction kettle described above were added 40.5 grams (0.25 mole) of anhydrous ferric chloride, and 200 ml of mixed isomer xylene. The reaction mixture was stirred and heated to 120° under a slow stream of nitrogen for 3 hours. The reaction mixture was cooled to room temperature, and 10 grams (0.36 g. atom) of powdered aluminum were added. After 30 minutes, 46.5 grams (0.25 mole) of ferrocene and 100 grams (0.25 mole) of anhydrous aluminum chloride were added. The reaction mixture was purged with nitrogen and heated to 140° C. for 6 hours. The reaction mixture was cooled and quenched with ethanol in the usual manner.

The reaction mixture was then transferred to a flask containing 500 ml of ice/water and 4 grams of ascorbic acid. The aqueous phase was separated and the organic phase extracted with 150 ml of water. The combined aqueous solutions were extracted with three 250 ml portions of cyclohexane and then filtered to remove residual aluminum powder. The reaction product was precipitated from the aqueous phase as the hexafluorophosphate salt by addition of 140 grams of 60% hexafluorophosphoric acid. The reaction product was isolated by extraction with 300 ml, 100 ml and 50 ml portions of dichloromethane. This salt was crystallized from the combined dichloromethane solutions by addition of 1 liter of cyclohexane. The crystalline solids were removed by vacuum filtration, and dried under vacuum. Approximately 153.2 grams (0.41 mole) of product were obtained, for a yield of 165% based on ferrocene, or 82% based on total iron.

EXAMPLE 5

Preparation of cyclopentadienyliron (II) cumene hexafluorophosphate from ferrocene and ferrous chloride; an example of use of a Lewis acid combination. The reaction equations were as follows:

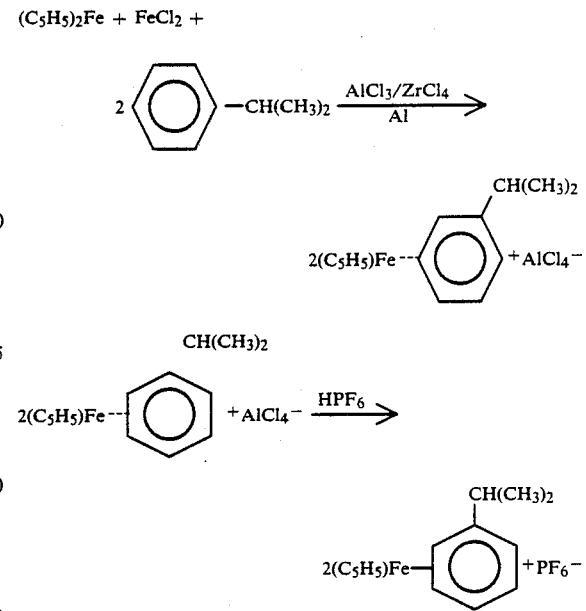

To the previously described reaction kettle were added 46.5 grams (0.25 mole) of ferrocene, 6.75 grams (0.25 g. atom) of aluminum powder, 100 grams (0.75 mole) of anhydrous aluminum chloride, 31.7 grams (0.25 mole) of anhydrous ferrous chloride, and 300 ml of cumene. The reaction mixture was purged with nitrogen, and 6.0 grams (0.025 mole) of anhydrous zirconium tetrachloride were added. The reaction mixture was heated to 100° C. for 3 hours. The reaction mixture was then cooled and quenched by slow addition of 200 ml of absolute ethanol.

The reaction mixture was added to 500 ml of ice/water followed by addition of 100 ml concentrated hydrochloric acid and an additional 300 ml of water. The mixture was filtered to remove unreacted aluminum, and the aqueous phase was removed. The organic phase was extracted with 100 ml of water. The aqueous solutions combined, and extracted with three 200 ml portions of cyclohexane. The reaction product was precipitated from the combined aqueous solutions by addition of 81.5 grams (0.5 mole) of ammonium hexafluorophosphate. The resultant yellow solid was removed by vacuum filtration, rinsed with 200 ml of water and three 100 ml portions of ethyl ether, and dried under vacuum. Approximately 96.8 grams (0.25 mole) of product were obtained, for a yield of 100% based on ferrocene or 50% based on total iron.

COMPARATIVE EXAMPLE 6

Control reaction for Example 5 was run in the absence of ferrous chloride.

The reaction was run as in Example 5, except that the ferrous chloride was omitted. The reaction was quenched and the product was isolated in the same manner as in Example 5. The product was precipitated, filtered and dried as in Example 5. Approximately 41.6 grams of an impure yellow-green solid was obtained, for a yield of 43% based on ferrocene.

EXAMPLE 7

Preparation of cyclopentadienyliron (II) (xylenes) hexafluorophosphate by reaction of lithium cyclopentadienide with ferrous chloride. The reaction equations were as follows:

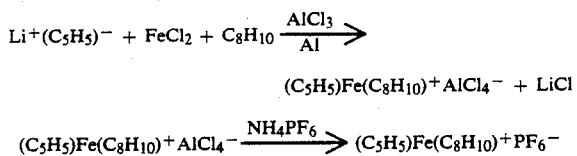

To the reaction kettle described above were added 67 grams (0.5 mole) of anhydrous aluminum chloride, 6.75 grams (0.25 g. atom) of powdered aluminum, 31.7 grams (0.25 mole) of anhydrous ferrous chloride, and 200 ml of mixed isomer xylene. The mixture was stirred and purged with nitrogen. A suspension of 18 grams (0.25 mole) of lithium cyclopentadienide in 200 ml of xylenes was prepared and added to the reaction vessel and rinsed with an additional 100 ml of xylenes. The reaction mixture was again purged with nitrogen and then heated to 140° C. and maintained at this temperature for 6 hours. The reaction mixture was then cooled to 50° C. and quenched by the slow addition of 200 ml of absolute ethanol.

The reaction mixture was then poured into 500 ml of ice/water, forming suspended solids. The suspended solids were then removed by vacuum filtration. The filtrate was transferred to a separatory funnel, and the aqueous layer was removed and extracted with 300 ml of cyclohexane. The reaction product was precipitated from the aqueous phase as the hexafluorophosphate salt by addition of 41 grams (0.25 mole) of ammonium hexafluorophosphate in 50 ml of water. The resulting yellow solid was removed by vacuum filtration, rinsed with water and ether, and dried under vacuum. The yield of the desired product was 50.5 grams (0.14 mole) or 54% of the theoretical yield.

EXAMPLE 8

Preparation of cyclopentadienyliron (II) cumene hexafluorophosphate by reaction of lithium cyclopentadienide and ferrous chloride. The reaction equations were:

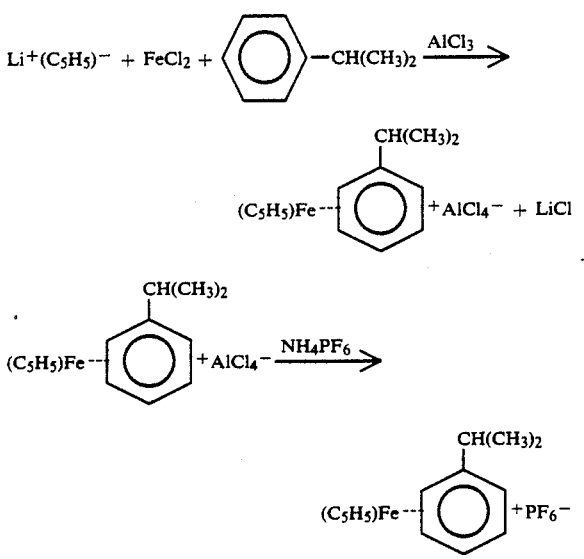

To the reaction kettle described above were added 67 grams (0.5 mole) of anhydrous aluminum chloride, 6.75 grams (0.25 g. atom) of powdered aluminum, 31.7 grams (0.25 mole) of anhydrous ferrous chloride, and 200 ml of cumene. The reaction mixture was purged with nitrogen. A slurry of 18 grams (0.25 mole) of lithium cyclopentadienide in 250 ml of cumene was added to the reaction mixture. The nitrogen purge was continued, while the reaction mixture was heated to a temperature of 110° C. and maintained at this temperature for approximately 3 hours. The reaction mixture was then cooled and quenched by the slow addition of 200 ml of absolute ethanol.

The reaction mixture was then added to 500 ml of water and vacuum filtered to remove solids. The aqueous phase was separated and extracted with 100 ml of cyclohexane. The reaction product was precipitated from the aqueous phase by addition of 44 grams of ammonium hexafluorophosphate in 100 ml of water. The resulting yellow solids were removed by vacuum filtration, rinsed with water and ether, and dried under vacuum. Approximately 53 grams (0.14 mole) of product was obtained, for a yield of 55% of theoretical.

EXAMPLE 9

Preparation of cyclopentadienyliron (II) cumene hexafluoroantimonte by reaction of sodium cyclopentadienide and ferrous chloride. The reaction equations were:

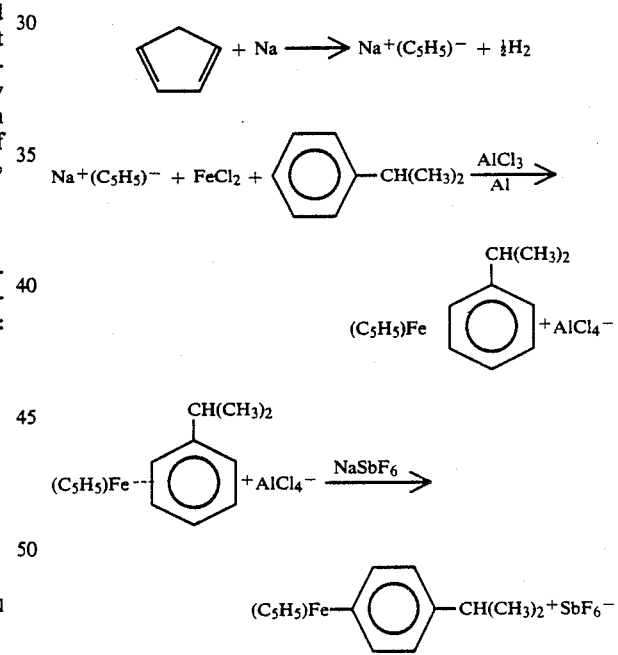

In the reaction kettle described above, a mole of sodium cyclopentadienide was prepared by slow addition of 1.2 moles of freshly prepared cyclopentadiene to 1 g. atom of sodium dispersion (50% in paraffin wax, Aldrich, Milwaukee, WI) in 1 liter of cumene, and 250 ml of tetrahydrofuran. When addition was complete, the reaction mixture was heated to 70° C. for 4 hours. The reflux condenser was then replaced with a distillation head, and the tetrahydrofuran removed by distillation. The reaction mixture was then allowed to cool, and 114 grams (0.9 mole) of anhydrous ferrous chloride, 13.5 grams (0.5 g. atom) of powdered aluminum, and 266 grams (2.0 moles) of anhydrous aluminum chloride were added. The reaction mixture was heated to 100° C. and maintained at this temperature for 3 hours. The reaction mixture was then cooled, and quenched by the slow addition of 500 ml of absolute ethanol. After 30 minutes, the reaction mixture was poured into 2 liters of ice/water. The cumene layer (organic layer) was separated and the aqueous layer was vacuum filtered to remove solids. The aqueous filtrate was extracted with 300 ml of cyclohexane. The product was precipitated as the hexafluoroantimonate salt by addition of 210 grams of sodium hexafluoroantimonate as a slurry in 300 ml of water. The precipitate that formed was isolated by extraction with 600 ml of dichloromethane. The dichloromethane layer was separated and the aqueous solution reextracted with two 200 ml portions of dichloromethane. The dichloromethane solutions were combined and extracted with 250 ml of water. The product was precipitated as an oil from dichloromethane solution by addition of 2 liters of cyclohexane. Cyclohexane was decanted from the oil, and 500 ml of ethyl ether were added, solidifying the product. The product was removed by vacuum filtration, rinsed with ether, and dried under vacuum. Approximately 268 grams (0.56 mole) of product was obtained, for a yield of 62% based on ferrous chloride.

Various modifications and alterations of this invention will become apparent to those skilled in the art without departing from the scope and spirit of this invention, and it should be understood that this invention is not to be unduly limited to the illustrative embodiments set forth herein.

I claim:

1. A method for preparing a cyclopentadienyliron (II) arene cation complex salt comprising the steps:
   a) providing a mixture comprising ferrocene, an arene, a Lewis acid, and a ferrous salt in an amount sufficient to effect complete reaction,
   b) isolating the product of said reaction.
2. The method as recited in claim 1 wherein said mixture further comprises an inert, non-polar diluent.
3. The method as recited in claim 2 wherein said mixture further comprises a reducing metal selected from the group consisting of aluminum, magnesium, and zinc.
4. The method as recited in claim 3 wherein said cyclopentadienyliron (II) cation complex salt has the formula:

$$((Cp)-Fe-(Ar))^+{}_b X^{b-}$$

wherein
Cp is an eta$^5$ complexed cyclopentadienyl anion, or an eta$^5$ complexed indenyl anion,
Ar is an eta$^6$ complexed arene,
X is an anion of valence b, and
b is an integer 1, 2, or 3.
5. The method of claim 4 wherein said Lewis acid is selected from a first group consisting of aluminum chloride, aluminum bromide, boron chloride, gallium chloride and a combination of a Lewis acid selected from said first group and a Lewis acid selected from a second group consisting of titanium tetrachloride, zirconium tetrachloride, hafnium tetrachloride and tin tetrachloride wherein said second Lewis acid, when present, does not exceed a 0.2:1 ratio between said acid and ferrocene.
6. A method of claim 1 for preparing cyclopentadienyliron (II) arene cation complex salt further comprising:
   a) quenching the reaction of said reacting step by hydration of said Lewis acid prior to isolating the resulting product.
7. The method of claim 6 wherein said quenching step further includes:
   a) adding absolute alcohol, wherein said absolute alcohol is methanol, ethanol or isopropanol;
   b) providing external cooling; and
   c) transferring said reaction mixture to an aqueous mixture.
8. The method of claim 7 wherein said mixture comprises at least 1 mole of ferrocene, at least 2 moles of arene, at least 0.2 moles of ferrous salt, at least 1 mole of a Lewis acid, at least 0.1 mole of a reducing metal and optionally, an inert, non-polar diluent.
9. The method of claim 7 wherein said mixture comprises of at least 0.25 mole of ferrocene, 200-300 ml of arene, wherein said arene is one of xylene or cumene, at least 0.75 mole of anhydrous aluminum chloride, at least 0.25 mole of anhydrous ferrous chloride and at least 0.25 g. atom of powdered aluminum.
10. The method of claim 9 for providing cyclopentadienyliron (II) arene cation complex salt further comprising the step:
   a) adding $PF_6^-$ or $SbF_6^-$ to said resulting product prior to said isolating step wherein
   one of cyclopentadienyliron (II) xylene+$PF_6^-$, cyclopentadienyliron (II) cumene+$PF_6^-$, cyclopentadienyliron (II) xylene+$SbF_6^-$ or cyclopentadienyliron (II) cumene+$SbF_6^-$ is the product salt precipitated; and
   b) purifying said precipitated product.
11. The method of claim 7 wherein said ratio of ferrocene to anhydrous aluminum chloride to anhydrous ferrous chloride to powdered aluminum is at least 1:3:1:1.
12. A method for preparing a cyclopentadienyliron (II) cation complex salt comprising the steps:
   a) reacting a mixture comprising a metal cyclopentadienide salt, an arene in the presence of a Lewis acid, and with sufficient ferrous salt to effect completion of the reaction;
   b) isolating the resultant product.
13. The method of claim 12 wherein said reaction of said reacting step takes place under an inert atmosphere.
14. The method of claim 13 wherein said reaction mixture further comprises an inert, non-polar diluent.
15. The method of claim 14 wherein said reaction mixture further comprises a reducing metal selected from the group consisting of aluminum, magnesium, and zinc.
16. The method of claim 15 wherein said cyclopentadienide salt has the general formula:

$$M^{b+}(Cp)_b{}^-$$

wherein
M is a metal cation of valence b,
b is an integer 1, 2, or 3, and
Cp is a cyclopentadienyl anion, or an indenyl anion.
17. The method of claim 16 wherein said Lewis acid is selected from the group consisting of aluminum chloride, aluminum bromide, boron chloride, and gallium chloride.

18. The method of claim 12 further comprising the step:
a) quenching the reaction of said reacting step by hydration of said Lewis acid prior to isolating the resulting product.

19. The method of claim 18 wherein said quenching step further comprises:
a) adding absolute alcohol, wherein said absolute alcohol is at least one of methanol, ethanol or isopropanol;
b) providing external cooling;
c) transferring said reaction mixture to an aqueous mixture.

20. The method of claim 16 wherein said mixture comprises at least 1 mole of metal cyclopentadienide, at least 1 mole of arene, at least 0.5 mole of ferrous salt, at least 0.5 mole of a Lewis acid, at least 1 mole of a reducing agent wherein said reducing agent is one of aluminum, magnesium or zinc and optionally, an inert, nonpolar diluent.

21. The method as recited in claim 16 wherein said cyclopentadienyliron (II) cation complex salt has the formula:

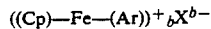

wherein
Cp is an eta$^5$ complexed cyclopentadienyl anion, or an eta$^5$ complexed indenyl anion;
Ar is an eta$^6$ complexed arene;
X is an anion of valence b; and
b is an integer 1,.2 or 3.

22. The method of claim 16 wherein said mixture comprises of at least 0.5 mole of anhydrous aluminum chloride, at least 0.25 g. atom of powdered aluminum, at least 0.25 mole of anhydrous ferrous chloride, at least 200 ml of an arene, wherein said arene is one of xylene or cumene.

23. The method of claim 22 for providing cyclopentadienyliron (II) arene cation complex salt further comprising:
a) adding at least 0.25 mole of ammonium hexafluorophosphate or sodium hexafluoroantimonate to said product mixture prior to said isolating step, wherein one of cyclopentadienyliron (II) xylene hexafluorophosphate, cyclopentadienyliron (II) cumene hexafluorophosphate, cyclopentadienyliron (II) xylene hexafluoroantimonate or cyclopentadienyliron (II) cumene hexafluoroantimonate is precipitated;
b) isolating said precipitated product.

* * * * *

UNITED STATES PATENT AND TRADEMARK OFFICE
CERTIFICATE OF CORRECTION

PATENT NO. : 5,059,701
DATED : October 22, 1991
INVENTOR(S) : Keipert It is certified that error appears in the above-identified patent and that said Letters Patent is hereby corrected as shown below:

Abstract, line 9, "anad" should be --and--.

Col. 1, line 6, insert the number --0-- before the "7".

Col. 6, line 9, insert the words -- the present-- before the word "invention".

Col. 13, line 44, "$AlC_4$" should be --$AlCl_4$--.

Col. 16, line 44, insert the word --were-- before the word "combined".

Col. 18, line 25, "afluoroantimonte" should be --afluoroantimonate--.

Col. 20, line 32, "$PF_6$" should be --$PF_6$--.

Col. 22, line 6, "." should be deleted before the 2.

Signed and Sealed this

Twenty-seventh Day of April, 1993

*Attest:*

MICHAEL K. KIRK

*Attesting Officer*    *Acting Commissioner of Patents and Trademarks*